United States Patent [19]

Kwak et al.

[11] Patent Number: 5,089,636

[45] Date of Patent: Feb. 18, 1992

[54] METHOD OF ISOLATING GINKGOLIDES FROM THE LEAVES OF THE GINKGO TREE AND PURIFYING THEM

[75] Inventors: Wie J. Kwak, Seoul; Hwa K. Park, Kyonggi-do; Key B. Oh, Kyongsangnam-do, all of Rep. of Korea

[73] Assignee: Sunkyong Industries Ltd., Rep. of Korea

[21] Appl. No.: 539,424

[22] Filed: Jun. 15, 1990

[30] Foreign Application Priority Data

Jun. 16, 1989 [KR] Rep. of Korea .................. 89-8340

[51] Int. Cl.$^5$ ............................................ C07D 493/00
[52] U.S. Cl. ..................................................... 547/297
[58] Field of Search ............................................ 549/297

[56] References Cited

PUBLICATIONS

Okabe et al., J. Chem. Soc. (5) 2201 (1967).
Weinges et al., Liebigs Ann. Chem. 1987, No. 5, pp. 521-526, English translation.
Maruyama et al., Tetrahedron Letters, No. 4, pp. 299-302, 1967.
Nakanishi CA 53738m, vol. 67, 1967.
"Studies on the constituents of 'Ginkgo' Leaves", Furukawa, Scientific Papers of the Institute of Physical and Chemical Research, 1932, vol. 19, pp. 27-38.
"The Ginkgolides", Nakanishi, Pure Applied Chemistry, 8, pp. 89-113, 1967.

*Primary Examiner*—Jane T. Fan
*Attorney, Agent, or Firm*—Michael L. Dunn

[57] ABSTRACT

A method of isolating ginkgolides from the leaves of the Ginkgo tree which is characterized by a series of steps as follows:

(a) Adjusting the pH of an aqueous solution of an extract of the leaves of the Ginkgo tree to the range of 7 to 9 by adding an alkaline aqueous solution, (b) Extracting the aqueous solution treated as above with lower acetates, lower ketones or benzenes, separate the solution into a layer of aqueous solution and a layer of organic solvent, dehydrating and drying the layer of organic solvent, and obtaining a powder, (c) Adjusting the pH of the layer of aqueous solution separated in step (b), to the range of 1 to 3 by adding an acidic aqueous solution, extracting the layer of aqueous solution treated as above with lower ethers or chloroforms, dehydrating and drying the obtained extract, (d) Dissolving the dry powder obtained the step (b) and the residue obtained in the step (c) in a lower alcohol, (c) Adding an aqueous solution of lead acetate to the solution obtained in the step (d), removing the precipitate, concentrating the filtrate, and obtaining a powder mixture of ginkgolides.

13 Claims, No Drawings

METHOD OF ISOLATING GINKGOLIDES FROM THE LEAVES OF THE GINKGO TREE AND PURIFYING THEM

DETAILED DESCRIPTION OF THE INVENTION

The present invention relates to a method of isolating the effective physio-active substances ginkgolides from the leaves of the Ginkgo tree and purifying them, on a large scale.

It is known that there are many effective physio-active substances contained in the Ginkgo tree: the phenolic compounds ginkgol, bilobol, ginkgolic acid, etc. in the fruit; cyanogenetic glycosides, amino acids, etc. in the seeds; aromatic compounds, particularly phenolic compounds flavonoid glycosides and simple flavonoids—kaempferol, quercetin, isorhamnetin, luteolin, etc.—, terpenoid compounds ginkgolides and bilobalid, etc. in the leaves.

Particularly, as for the terpenoid compounds among the aforesaid compounds present in the leaves of the Ginkgo tree, the lactone compounds were first identified by S. Furukawa in 1929 (Sci. Papers Inst. Phys. Chem Res. Tokyo 19. 27 (1932)); the ginkgolides were first isolated from the roots of the Ginkgo tree by K. Nakanishi in 1967 (Pure Appl. Chem. 7. 89 (1967), Tetrahedron Letter, 4. 299 (1967)), their structures were determined and named Ginkgolide A, B, C and M; in 1967, K. Okabe et al. also ascertained the presence of the ginkgolides in the leaves of the Ginkgo tree (J. Chem. Soc.(5) 2201 (1967)).

Another ginkgolide, Ginkgolide J, was later identified by K. Weing in 1987 (Lieb. Ann. Chem. 521–526 (1987)) and it chemical structural formula is as follows:

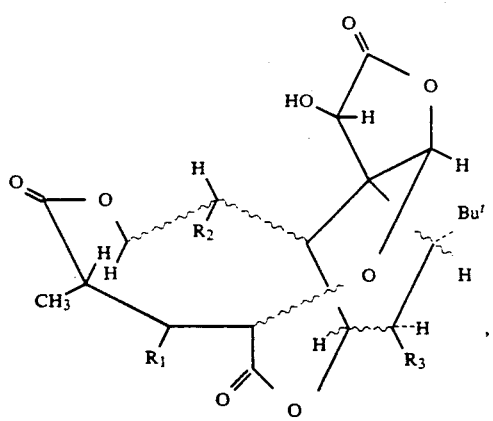

in the above structural formula

| Kind of ginkgolides | R1   | R2  | R3  |
|---------------------|------|-----|-----|
| Ginkgolide A        | —OH  | —H  | —H  |
| Ginkgolide B        | —OH  | —OH | —H  |
| Ginkgolide C        | —OH  | —OH | —OH |
| Ginkgolide M        | —H   | —OH | —OH |
| Ginkgolide J        | —OH· | —H  | —OH |

Recently, it has been found that, by their competitive reaction with platelet-activating factor (PAF, PAF-acether, AGEPC), such ginkgolides have effects on many PAF-acether-induced diseases such as asthma, bronchitis, dementia senilis, allergy, cardiac disorders, shock related to organ transplantation, rheumatic diseases, etc. and a broad range of other circulatory system diseases (P. Braquet, Drug of the Future, 12, 643, 1987).

A good method for isolating ginkgolides from the leaves of the Ginkgo tree has not yet been found, because there is such a small quantity of ginkgolides present in the leaves of the Ginkgo tree and it is difficult to isolate them.

Consequently, the purpose of the present invention is to provide a method of isolating the effective physio-active ginkgolide substances from the leaves of the Ginkgo tree and purifying them, at a high yield.

BRIEF DESCRIPTION OF THE INVENTION

The present invention is a method of isolating ginkgolides from the leaves of the Ginkgo tree which is characterized by a series of processes steps as follows:

1. The pH of an aqueous solution of an extract of the leaves of the Ginkgo tree is adjusted to the range of 7 to 9 by adding an alkaline aqueous solution, 2. The aqueous solution treated as above is extracted with lower acetates, lower ketones or benzenes, and the solution is separated into a layer of aqueous solution and a layer of organic solvent, and the layer of organic solvent is dehydrated and dried to and obtain a powder, 3. The pH of the layer of aqueous solution, separated in step 2. is adjusted to the range of 1 to 3 by adding an acidic aqueous solution. The layer is extracted with lower ethers of chloroforms, dehydrated and dried to obtain the extract, 4. The dry powder obtained in step 2 and the residue obtained in the step 3 is dissolved in a lower alcohol, and 5. An aqueous solution of lead acetate is added to the solution obtained in step 4., the precipitate removed, and the filtrate concentrated, to obtain a mixture of ginkgolide powders.

In the present invention, the aqueous solution of an extract of the leaves of the Ginkgo tree is prepared by extracting a dry powder of the leaves of the Ginkgo tree in lower alcohols or lower ketones at the temperature of 50° C. to 100° C. for 5 to 6 hours.

Besides, the present invention also covers a method of purifying the mixture ginkgolide powders obtained according to the afore-said method which is characterized by the processes of passing the afore-said powder mixture through an adsorption column of activated charcoal and silica gel using a mixture solvent mixture of lower acetates and lower alcohols and putting the obtained residue through separation recrystallization using absolute alcohol and an aqueous solution of acetone.

On the other hand, it is possible to purify the powdered mixture of ginkgolides, obtained according to the present invention by the processes of dissolving the afore-said powder mixture in lower ketones or lower alcohols, adding distilled water, centrifuging the solution thus treated and putting the obtained residue through separation recrystallization using absolute alcohol and an aqueous solution of acetone.

DETAILED DESCRIPTION OF THE INVENTION

First, a powder of dried and pulverized fresh leaves of the Ginkgo tree is put in an aqueous solution of lower alcohols or lower ketones and then extracted at the temperature of 50° C. to 100° C. for 5 to 6 hours; the filtrate thus obtained is mixed with an appropriate amount of carbon tetrachloride, which is water-insoluble, then agitated and then separated.

The pH of the layer of aqueous solution separated above is adjusted to the range of 7 to 10, preferably 7 to 9, by adding an aqueous solution of sodium hydroxide, then extracted with lower ketones, lower acetates or benzene, which are water-insoluble, then dehydrated by adding anhydrous sulfates, calcium carbonate or phosphates and then dried by depression or vacuum.

The pH of the remaining layer of aqueous solution in the afore-said process is adjusted to the range of 1 to 3 by adding diluted hydrochloric acid and then separated with a water-insoluble solvent; the layer of organic solvent thus obtained is vacuum dried and then mixed with the powder in the afore-said step; in this step, ether, chloroform or dichloromethane is preferable as a separation solvent.

The powder obtained in the previous step is dissolved in an aqueous solution of lower alcohols and then separated with hexane or cyclohexane to get rid of the remaining lipidic substances; to the filtrate thus obtained, an aqueous solution of lead hydroxide is added; the filtrate thus treated is agitated and let to stand; the precipitate thus formed is filtered; the filtrate thus obtained is concentrated and dried to obtain, a powder mixture with a high content of ginkgolides.

To purify the powder mixture obtained according to the present invention, the powder mixture is passed through an adsorption column thereby getting rid of the remaining phenolic substances. The filtrate passed through the adsorption column is dried by evaporation, then dissolved in a small amount of anhydrous ethanol and let to stand at low temperature; thus, a white amorphous solid is obtained.

The powder mixture may also be dissolved in an aqueous solution of acetone and then centrifuged; the powder thus obtained is dissolved in an aqueous solution of alcohols and then let to stand at low temperature; thus, white crystalline ginkgolides are obtained.

The white solid obtained in the final purification is a mixture comprising pure Ginkgolide A, B and C and a very small amount of Ginkgolide M and J without phenolic substances; the respective ginkgolides can be isolated by separation recrystallization using a mixture solvent of acetone and water, and identified by thin-layer chromatography or liquid chromatography and hydrogen nuclear magnetic resonance spectrum.

To describe the present invention in further detail, examples are given as follows:

EXAMPLE 1

To 50 liters of 70% acetone aqueous solution, 10 kg of dried powder of the leaves of the Ginkgo tree is added. The mixture is extracted two times for 5 hours at 80° C. with an inverse flow and the filtered.

The filtrate is concentrated to 7 liters and then extracted three times with 2 liters of carbon tetrachloride each time, thereby getting rid of the remaining chlorophylls. The pH of the remaining layer of aqueous solution is adjusted to 7.5 by adding 1-N aqueous solution of sodium hydroxide. The layer of aqueous solution treated as above is extracted five times with 3 liters of ethylacetate each time, then dehydrated with sodium sulfate, then concentrated and dried.

The pH of the remaining layer of aqueous solution obtained after the afore-said process is adjusted to 3.5 by adding 1-N aqueous solution of hydrochloric acid. The layer of aqueous solution treated a above is extracted five times with 3 liters of ethylether per each extraction, then dehydrated and vacuum dried. The powder thus obtained is mixed with the powder obtained by the afore-said process; thereby, 120 g of yellow solid powder is obtained.

The afore-said yellow solid powder is dissolved in 150 ml of ethanol, then mixed with 16 g of activated charcoal, then agitated and filtered. The filtrate is vacuum dried: thereby, 90 g of mixture powder with a high content of ginkgolides is obtained.

EXAMPLE 2

To 50 liters of ethylacetate, 10 kg of dried powder of the leaves of the Ginkgo tree is added. The mixture is extracted two times for 6 hours at 80° C. with an inverse flow and then filtered.

The filtrate is completely concentrated, then mixed with 5 liters of 30% methanol, then agitated and let to stand at 50° C., and then filtered, thereby getting rid of insoluble substances. The filtrate is extracted two times with 2 liters of cyclohexane a time, thereby getting rid of lipidic substances. The pH of the remaining layer of aqueous solution is adjusted to 7.5 by adding 1-N aqueous solution of sodium hydroxide. The layer of aqueous solution treated as above is extracted five times with 3 liters of water a time and five times with 3 liters of saturated methylethylketone a time, then dehydrated with anhydrous sodium sulfate, then concentrated and dried.

The pH of the remaining layer of aqueous solution obtained after the afore-said process is adjusted to 2.5 by adding 1-N aqueous solution of hydrochloric acid. The layer of aqueous solution treated as above is extracted three times with 3 liters of chloroform a time, then dehydrated and dried. The solid powder thus obtained is mixed with the powder obtained by the afore-said process; thereby, 125 g of yellow solid powder is obtained.

The afore-said yellow solid powder is dissolved in 150 ml of ethanol, then mixed with an aqueous solution of lead acetate, then agitated and let to stand, and filtrated, thereby getting rid of the formed precipitate. The filtrate is concentrated and dried; thereby, 60g of mixture powder with a high content of ginkgolides is obtained.

EXAMPLE 3

To the 50 liters of methanol, 10 kg of dried powder of the leaves of the Ginkgo tree is added. The mixture is extracted two times for 6 hours at 70° C. with an inverse flow and then filtrated.

The filtrate is concentrated to 5 liters and then extracted two times with 2 liters of carbon tetrachloride a time, thereby getting rid of the layer of organic solvent. The pH of the remaining layer of aqueous solution is adjusted to 8.5 by adding 1-N aqueous solution of sodium hydroxide. The layer of aqueous solution treated as above is separated five times with 3 liters of benzene a time, and then the layer of benzene thus obtained is dehydrated with ammonium sulfate and dried. The pH of the remaining layer of aqueous solution is adjusted to 2.0 by adding 1-N aqueous solution of hydrochloric acid. The layer of aqueous solution treated as above is extracted three times with 2 l of dichloromethane a time, and the layer of organic solvent thus obtained is dehydrated and dried. The powder thus obtained is mixed with the powder obtained by the afore-said process; thereby, 90 g of brown powder is obtained.

The afore-said brown powder is dissolved in 120 ml of acetone, then mixed with an aqueous solution of lead acetate, then agitated and let to stand, and filtered, thereby getting rid of the formed precipitate. The filtrate is concentrated and dried; thereby, 55 g of mixture powder with a high content of ginkgolides is obtained.

EXAMPLE 4

100 g of the solid substance obtained in the afore-said EXAMPLE 1 is put in 100 ml of acetone and then let to pass through an adsorption column filled with 50 g of activated charcoal and 1 kg of silicagel, thereby getting rid of the remaining phenolic substances and impurities in the afore-said process, the solvent used is a mixture solvent of ethylacetate and methanol in the ratio of 15 to 1; ginkgolides are identified by thin-layer chromatography [silicagel; cyclohexane-ethylacetate (50:50) as solvent; acetic anhydride spray yielding, after heating, a faint orange fluorescence at 365 nm]. The solution passed through the adsorption column is dried by evaporation; thereby, 18 g of whitish powder is obtained.

The afore-said whitish powder is completely dissolved in 50 ml of anhydrous ethanol at 60° C. and then let to stand at a low temperature for 10 hours; thereby, 10 g of white amorphous crystals, pure ginkgolides, are obtained.

The afore-said ginkgolides are a mixture comprising Ginkgolides A, B and C and a very small amount of Ginkgolides J and M. Each ginkgolide can be isolated by separation recrystallization with 50% aqueous solution of acetone.

EXAMPLE 5

100 g of the powder obtained in the afore-said EXAMPLES 1, 2 and 3 is dissolved in 200 ml of acetone. To the solution thus obtained, 800 ml of distilled water is slowly added with agitation. The whitish colloidal liquid thus formed is centrifuged.

After centrifuging, the supernatant fluid is removed, and the remaining substances are vacuum dried to obtain 65 g of brown solid powder.

The afore-said solid powder is completely dissolved in 50 ml of 30% methanol at 60° C. and then let to stand at a low temperature for 12 hours; thereby, 17.5g of white amorphous crystals, pure ginkgolides, are obtained.

The analysis by liquid chromatography (column: waters—Bondapak - $C_{18}$, length: 30 cm, diameter: 3.9 m, temperature: 25° C., solvent: mixture of water, methanol and tetrahydrofuran in the ratio of 75:20:10, flow rate: 1.5 ml/min, sensor: UV 210 nm) of the afore-said ginkgolides show that the ginkgolides are a mixture of 35% Ginkgolide A, 45% Ginkgolide B, 12% Ginkgolide C and 3% others.

By the separation recrystallization of the afore-said ginkgolides with anhydrous ethanol and 50% aqueous solution of acetone, each pure ginkgolide is obtained.

The results of analysis of each pure ginkgolide are as follows:

Ginkgolide A [melting point=308° C., Hydrogen Nuclear Magnetic Resonance Spectrum data (100 MHz, ppm): 1.20(S), 1.45(d), 2.0–2.5(m), 2.60 (dd), 2.99 (dd), 3.1111 (q); 5.05 (s), 5.13 (t), 5.38 (s), 6.20 (s); Infra-Red Adsorption Spectrum data ($vCO$:1802, 1776, 1764 cm$^{-1}$, $vOH$:3551, 3453 cm$^{-1}$)], Ginkgolide B [melting point: 300° C., Hydrogen Nuclear Magnetic Resonance Spectrum data (100 MHz, ppm): 1.22(s), 1 44(d), 2.1–2.7(m), 3.36 (q), 4.55 (d), 5.10 (d), 5.49 (s), 5.7 1 (s), 6.27 (s); Infra-Red Adsorption Spectrum data ($vCO$:1795, 1780 cm$^{-1}$, $vOH$:3454 cm$^{-1}$)], Ginkgolide C [melting point: 300° C., Hydrogen Nuclear Magnetic Resonance Spectrum data (100 MHz, ppm): 1.32(s), 1.45 (d), 2.14 (d), 3.36 (q), 4.53 (d), 4.73 (dd), 5.05 (d), 5.53 (s), 5.61 (d), 6.30 (s); Infra-Red Adsorption Spectrum data ($vCO$: 1785, 1763 cm$^{-1}$, $vOH$:3579, 3529 cm$^{-1}$)].

What is claimed is:

1. A method of isolating ginkgolides from the leaves of the Ginkgo tree which is characterized by a series of steps as follows:
   (a) Adjusting the pH of an aqueous solution of an extract of the leaves of the Ginkgo tree to the range of 7 to 9 by adding an alkaline aqueous solution,
   (b) Extracting the aqueous solution treated as above with a water insoluble organic solvent selected from the group consisting of lower alkyl acetate, acetone, lower alkyl ketone, benzene and lower alkyl benzenes separating the solution into a layer of aqueous solution and a layer of organic solvent, and obtaining a powder,
   (c) Adjusting the pH of the layer of aqueous solution separated in step (b), to the range of 1 to 3.5 by adding an acidic aqueous solution, extracting the layer of aqueous solution treated as above with a water insoluble organic solvent dehydrating and drying the obtained extract,
   (d) Dissolving the dry powder obtained the step (b) and the residue obtained in the step (c) in a lower alkyl alcohol,
   (e) Adding an aqueous solution of lead acetate to the solution obtained in the step (d), removing the precipitate, concentrating the filtrate, and obtaining a powder mixture of ginkgolides.

2. A method according to claim 1 wherein the aqueous solution of an extract of the leaves of the Ginkgo tree is prepared by extracting a dry powder of the leaves of the Ginkgo tree in a lower aklyl alcohol, a lower alkyl ketone or acetone at the temperature of 50° C. to 100° C. for 5 to 6 hours.

3. A method according to claim 1 wherein the layer of organic solvent in the step (b) is dehydrated and dried by adding an inorganic anhydrous sulfate salt, anhydrous calcium carbonate or an inorganic anhydrous phosphate salt.

4. A method according to claim 1 wherein the obtained powder mixture of ginkgolides is purified by passing the powder mixture through an adsorption column of activated charcoal and silica gel using a mixture solvent of lower alkyl acetates and lower alkyl alcohols and putting the obtained residue through separation recrystallization using anhydrous alcohol and an aqueous solution of acetone.

5. A method according to claim 1 wherein the obtained powder mixture of ginkgolides is purified by dissolving the mixture powder in lower alkyl ketones or lower alkyl alcohols, adding distilled water to the obtained solution, centrifuging the solution thus treated and then putting the obtained residue through separation recrystallization using anhydrous alcohol and an aqueous solution of acetone.

6. A method according to claim 1 wherein the organic solvent used in step (c) is selected from the group consisting of lower alkyl ether, chloroform and dichloromethane.

7. The method according to claim 1 wherein the solvent in step (b) is ethylacetate.

8. The method according to claim 1 wherein the organic solvent used in step (c) is ethyl ether.

9. The method according to claim 1 wherein the lower alkyl alcohol in step (d) is ethanol.

10. The method according to claim 1 wherein the layer of organic solvent in step (b) is dehydrated with sodium sulfate.

11. The method according to claim 7 wherein the solvent used in step (c) is ethyl ether.

12. The method according to claim 11 wherein the lower alkyl alcohol in step (d) is ethanol.

13. The method according to claim 12 wherein the layer of organic solvent in step (b) is dehydrated with sodium sulfate.

* * * * *